United States Patent [19]

Evans

[11] Patent Number: 5,201,881
[45] Date of Patent: Apr. 13, 1993

[54] JOINT PROSTHESIS WITH IMPROVED SHOCK ABSORPTION

[75] Inventor: David L. Evans, Bartlett, Tenn.

[73] Assignee: Smith & Nephew Richards Inc., Memphis, Tenn.

[21] Appl. No.: 744,425

[22] Filed: Aug. 13, 1991

[51] Int. Cl.⁵ ............................... A61F 2/38
[52] U.S. Cl. .................................... 623/20
[58] Field of Search ............ 623/16, 18, 20, 22, 623/23

[56] References Cited

U.S. PATENT DOCUMENTS

| | | | |
|---|---|---|---|
| Re. 31,865 | 4/1985 | Roux | 623/20 |
| 4,262,368 | 4/1981 | Lacey | 623/20 |
| 4,714,471 | 12/1987 | Grundei | 623/20 |
| 4,883,488 | 11/1989 | Bloebaum | 623/18 |
| 4,932,969 | 6/1990 | Frey et al. | 623/18 |

Primary Examiner—David Isabella
Attorney, Agent, or Firm—Pravel, Gambrell, Hewitt, Kimball & Krieger

[57] ABSTRACT

A joint prosthesis provides articulating prosthesis components that can deflect with respect to one another so that shock absorption is provided, lowering impact stresses. The components interface at articulating surfaces, and a gap is provided at a position away from the articulating surfaces, so that one of the components can flex into the gap area during use.

9 Claims, 4 Drawing Sheets

JOINT PROSTHESIS WITH IMPROVED SHOCK ABSORPTION

BACKGROUND OF THE INVENTION

1. Field of the Invention

The present invention relates to prosthetic devices and more particularly relates to an improved joint prosthesis that has improved shock absorption.

Even more particularly, the present invention relates to an improved joint prosthesis that includes articulating joint members, one of which flexes during impact to absorb shock, and wherein a gap between one joint component and another joint component allows deflection of one component into the gap area, to lessen impact stresses.

2. General Background

A tibial component for use in a knee prosthesis usually comprised of two parts, including a base plate which may be plastic or metal but which is usually metal, and a plastic plate which fits into or onto the base plate. The base plate carries some means for securing the base plate component to the bone, usually in the form of one or more screws or projections. Some base plates carry a pattern of fins which increases anchor strength and prevents rotation of the tibial component. The plastic plate can be prepared from high density polyethylene, and includes an upper articulating surface which is contoured to provide a surface on which the femur or femoral component can move.

Some patents (see eg. U.S. Pat. Nos. 4,865,407, 4,769,040 and 4,673,407 and European Patent No. 46926) discuss generally the problem of shock absorbing prostheses. U.S. Pat. Nos. 4,865,607 and 4,769,040 rely on a flexible metal or a reinforced resin layer to provide stress dissipating structure. U.S. Pat. No. 4,673,407 incorporates a spring to maintain a freely movable tibial prosthesis in position against the bone.

U.S. Pat. No. 4,865,607 describes a tibial plate which includes a reinforcement member capable of distributing the joint forces uniformally over the spongiosa so that it will not atrophy. The member is also subjected to flexure from the tibial plate which is also supported on a cut section of the corticalis surrounding the spongiosa. The reinforcing member can be planoconvex or biconvex in cross-section. The reinforcing member can be metal or a resin reinforced with carbon fibre. The reinforcing member is placed between the tibial plate and a conventional plastic plate member having a top surface shaped to engage with the femur or femoral prosthesis.

U.S. Pat. No. 4,822,362 describes a tibial prosthesis comprising a metal base plate contoured and dimensioned to correspond to the size and shape of the tibial plateau. The plate has a fixation pin and other projections which extend into the bone to fix and prevent rotation of the plate in use. A plastic cap is provided on the base plate and is made from high molecular weight polyethylene. The plastic cap has a concave upper surface for receiving the femur or a femoral prosthesis. The other surface of the plastic cap is shaped so as to form a snap-fit into the upper surface of the plate.

A tibial plateau prosthesis is described in U.S. Pat. No. 4,769,040. The prosthesis comprises a base plate which is shaped to fit onto the sectioned tibia. The base plate is flexible in the axial direction but stiff in the transverse direction. The distribution of stresses is said to mimic that of natural bone. A conventional articulating upper surface provided by high density polyethylene is present on the base plate.

U.S. Pat. No. 4,673,407 describes a prosthetic device, especially a tibial prosthesis, which comprises an implant for sealing onto the bone surface and an attachment element adapted to be secured to a portion of the base. The attachment member is connected to the implant by a connection member adapted to allow substantially unhindered movement of the implant relative to the attachment member. A low-modulus spring is operatively interposed between the connecting member and the implant so as to bias the implant against the bone surface. Movement of the implant allows substantially physiological loading of the bone in response to compression, shear, rotational and twisting forces.

U.S. Pat. No. 4,479,271 describes a tibial prosthesis which is adapted to promote the ingrowth of bone and/or tissue into the portion of the prosthesis which is in contact with the bone. The prosthesis comprises a bottom fibrous metal layer, an intermediate reinforcing metal layer and a molded, contoured polyethylene top layer.

U.S. Pat. No. 4,462,120 describes a total knee prosthesis. The tibial portion includes a metal base plate and two discrete pads which can be of different thicknesses and are made from polyethylene.

U.S. Pat. No. 4,268,920 discloses a knee joint endoprosthesis. The tibial and femoral components are arranged with respect to each other to permit a degree of rotation in the joint.

A knee joint endoprosthesis is described in European Patent No. 46926. The prosthesis has a tibial component which comprises two individual parts. One part carries a joint sliding surface, that is the surface which interacts with the femur or femoral prosthesis, and the other part carries an anchoring surface for anchoring the component to the bone. The two parts are connected to each other by the interposition of an elastic damping material for the transmission of compressive thrust and torsional forces. The connection between the two parts consists exclusively of the elastic damping material. The elastic damping material can be in the form of a plate or annular shaped or a plurality of elastic bodies which may be cylindrical, spherical or parallelapipedal shaped. The material may also vary in elasticity in different parts. The elastic material is preferably a silicone rubber.

French Patent No. 2585236 describes a total knee joint prosthesis. The tibial implant comprises a friction resistant plastic plate carried by a metal support. The bottom of the metal support has a series of dove-tail inserts to increase the surface of the support which is sealed to the tibia. The plastic plate has a lower projection which fits into a corresponding cavity in the support plate. The plastic plate when placed on the support is rendered immobile by the interaction of the projection and cavity.

European Patent No. 46926 discloses a knee prosthesis in which in the tibial component there is an elastic damping material. This material is placed between a metal support and a plastic part. The metal support has a surface for anchorage against the tibia. The plastic part has one surface shaped for sliding contact with the femur or a femoral prosthesis. Between the two parts is an elastic damping material which connects them together. The elastic damping material may be in the form of a plate or may be annular shaped.

SUMMARY OF THE PRESENT INVENTION

Joint replacement implants do not absorb impact loads as efficiently as a normal skeletal joint, because implants are made from materials which are relatively stiff and inelastic compared to articular cartilage and meniscal cartilage. One study by Hoshino and Wallace published in 1987 indicates that a conventional knee implant transmits peak loads which are seventy-six percent (76%) greater in magnitude than a normal knee. It is hypothesized that higher impact load transmission to the implant bone interface may cause microfractures of the bone, leading to subsidence of the implant. Subsidence of joint replacement implants is well-documented in the scientific literature.

If the magnitude of loads transmitted through the implant to the bone interface can be reduced to levels which are closer to normal, subsidence and its potential negative consequences may be reduced. Another potential benefit may be improved pain relief. Loads which are significantly higher than normal cause pain in bone (i.e. loads leading to fractures and loads from the distal end of cementless hip stems in vivo). If loads transmitted through joint replacement to bone can be reduced to normal levels, the patient may experience less pain, resulting in improved quality of life.

Another potential benefit of the present invention is to reduce wear of the implant over time. It is well-established that wear in dynamic mechanical systems is proportional to load. If loads are reduced, ceterus paribus, wear is reduced. The invention will reduce peak loads transmitted across the articular surface of a joint implant, thus the rate of wear of the articular surface will likely be reduced. A reduced wear rate will provide for longer implant life and reduced wear debris generation (less likelihood of adverse tissue reaction to wear particles).

The present invention reduces transmitted impact loads by means of using one part of the implant assembly as an energy absorber. The energy absorber is attached to another part of the implant. The attachment means and geometries of the parts of the implant allow, by means of a gap between the parts in the line of action of load transmission, one or both parts to flex when compression load is applied. The flexion of the parts requires strain energy to be accumulated in one or both parts. This reduces the amount of energy transmitted through the joint replacement device thus reducing the peak loads transmitted through the implant to the interface between the implant and bone.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
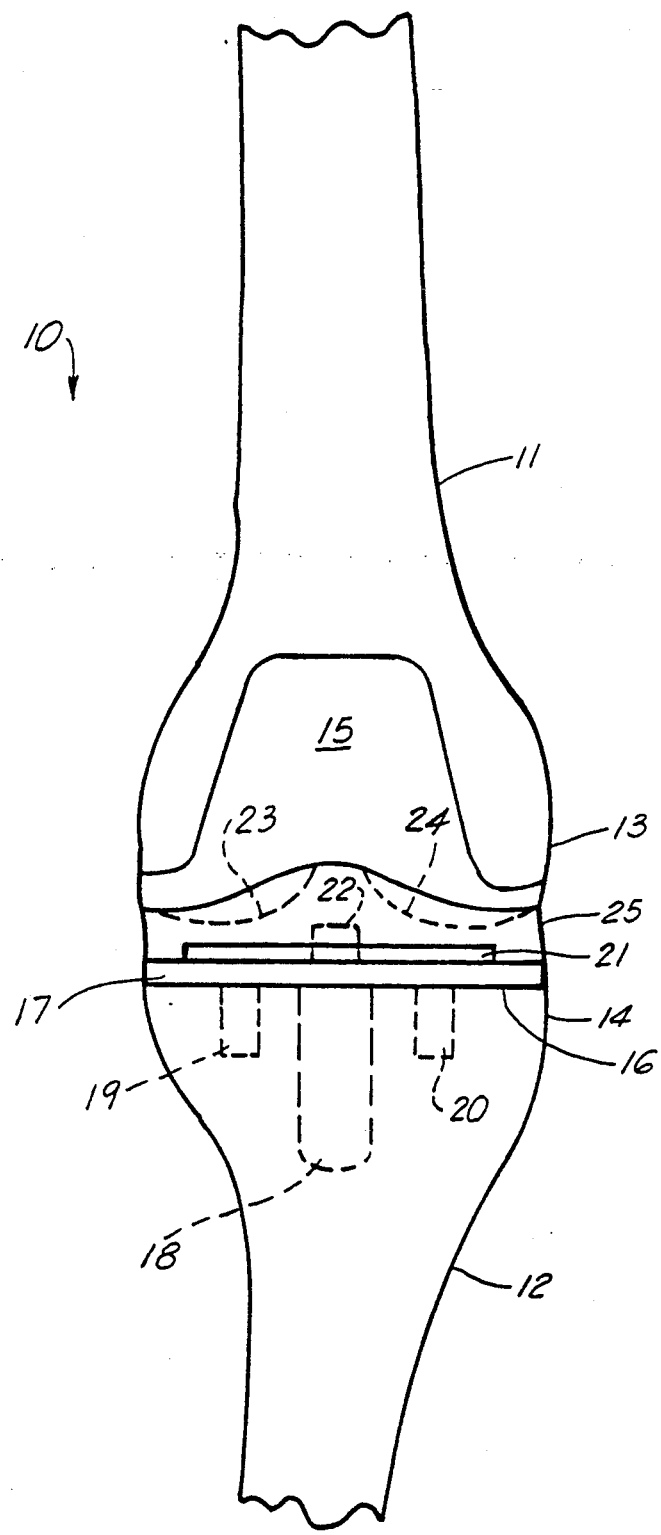
FIG. 1 is a schematic elevational view of the preferred embodiment of the apparatus of the present invention.
Figure 2:
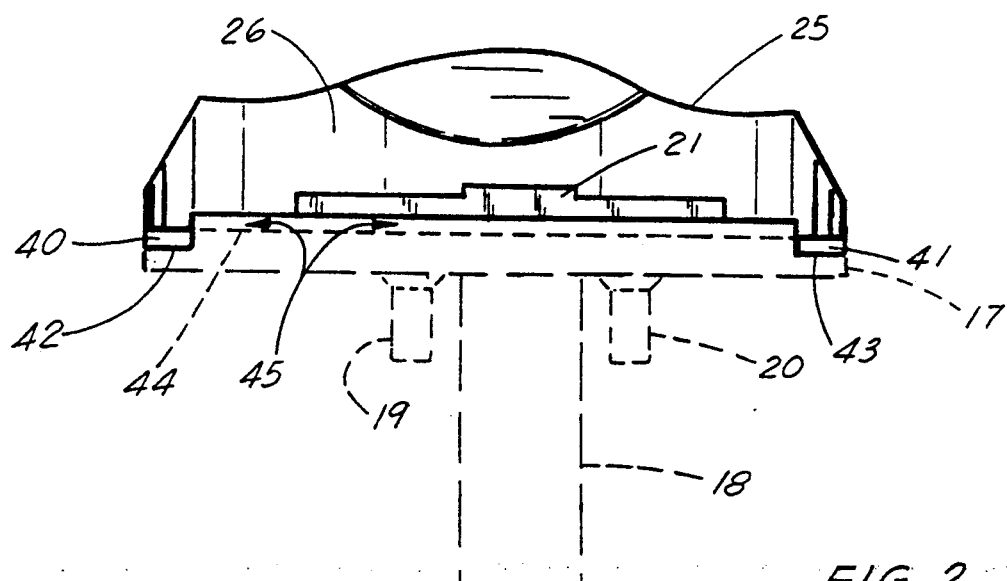
FIG. 2 is a front elevational fragmentary view of the preferred embodiment of the apparatus of the present invention showing the tibial component tray in phantom lines.
Figure 3:
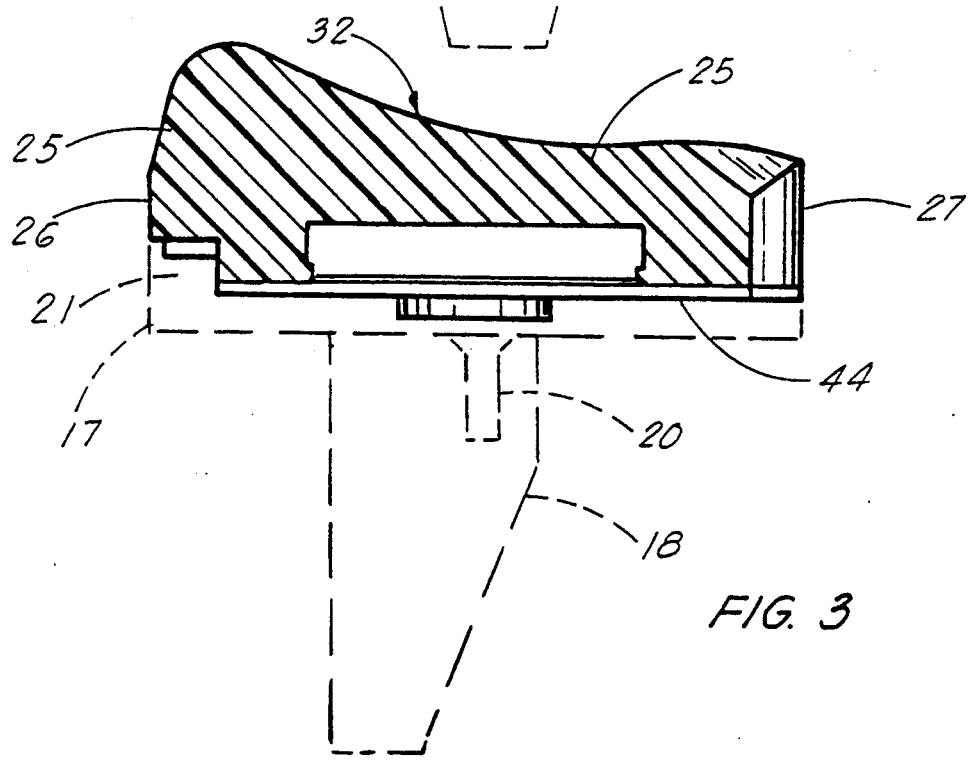
FIG. 3 is a side fragmentary and partially sectional view of the preferred embodiment of the apparatus of the present invention.
Figure 4:
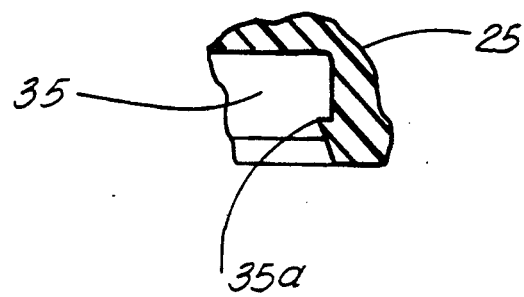
FIG. 4 is a fragmentary view of the preferred embodiment of the apparatus of the present invention.
Figure 5:
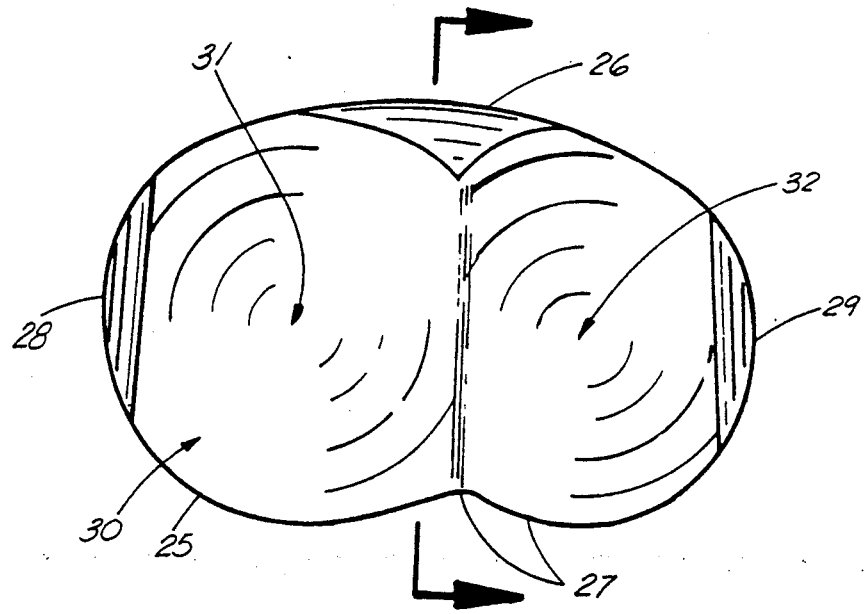
FIG. 5 is a top fragmentary view of the preferred embodiment of the apparatus of the present invention.

FIGS. 1 and 2-3 illustrate generally the preferred embodiment of the apparatus of the present invention designated generally by the numeral 10. In FIG. 1, a patient's femur 11 and tibia 12 are shown in an anterior view, and particularly illustrating the portion of the femur 11 and tibia 12 adjacent the knee joint. The joint prosthesis 10 of the present invention has been surgically installed in FIG. 1, showing the distal end 13 of femur 11 carrying femoral component 15 and the proximal end 14 of tibia 12 carrying a tibial component that includes tray 16 and tibial component insert 25.

The tibial component tray 16 includes a flat plate 17 with stem 18 extending downwardly therefrom. A pair of anchor posts 19, 20 are provided on opposite sides of stem 18. The anterior portion of plate 17 can provide an upwardly extending peripheral shoulder portion 21. A vertically upstanding flange 22 can also be provided on tibial component tray 16 for registration with tibial component insert 25 at socket 35 as will be described more fully hereinafter.

Tibial component insert 25 can be for example of a polymer material. The femoral component 15 can be of a polished metallic construction for example, providing a pair of curved and convexly shaped smooth articulating surfaces 23, 24. The tibial component insert 25 includes an anterior side 26, a posterior side 27 as well as medial 28 and lateral 29 side portions. A tibial articular surface 30 includes a pair of concavities 31, 32 that are shaped to receive the femoral articulating surfaces 23, 24. Tibial component insert 25 has a lower flat surface 34. Socket 35 is positioned centrally on the underside flat surface 34 of tibial component insert 25.

Socket 35 accommodates vertical flange 22 that extends upwardly on tibial component tray 16 so that the flange 22 registers with and tightly fits the socket 35 for purposes of forming a connection between the tibial component insert 25 and tibial component tray 16. A socket peripheral shoulder 35a can be provided to provide a tight fit between the socket 35 and flange 22.

A pair of spaced apart feet 36, 37 are provided on the medial and lateral sides of tibial component insert 25. Each foot 36, 37 is bordered by a vertical shoulder 38, 39 interiorly, and by lateral and medial sides 28, 29 exteriorly. The feet can best be seen in FIGS. 2 and 5-7.

Feet 36, 37 each provide respectively flat undersides that define bearing surfaces 36a, 37a which register upon and bear against upper surface 44 of plate 17 of tibial component tray 16. The area of upper surface 44 of plate 17 of tibial component tray 16 defines a flat surface between feet 36, 37 which is spaced vertically away from the flat surface underside 34 of insert 25 as seen in FIG. 2. This produces a gap 45 between top surface 44 of tibial component tray 16 and flat undersurface 34 of tibial component insert 25. When the femoral component 15 bears against the tibial component insert 25, some flexing occurs in the tibial component insert 25 and into the area of gap 45. The underside 34 of tibial component insert 25 bows downwardly toward the top surface 44 of tray 16.

Figure 6:
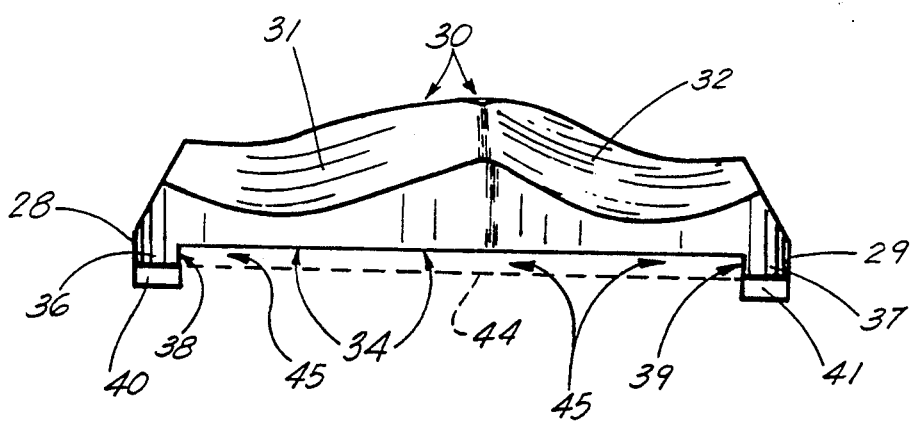
FIG. 6 is a rear fragmentary view of the preferred embodiment of the apparatus of the present invention.
Figure 7:
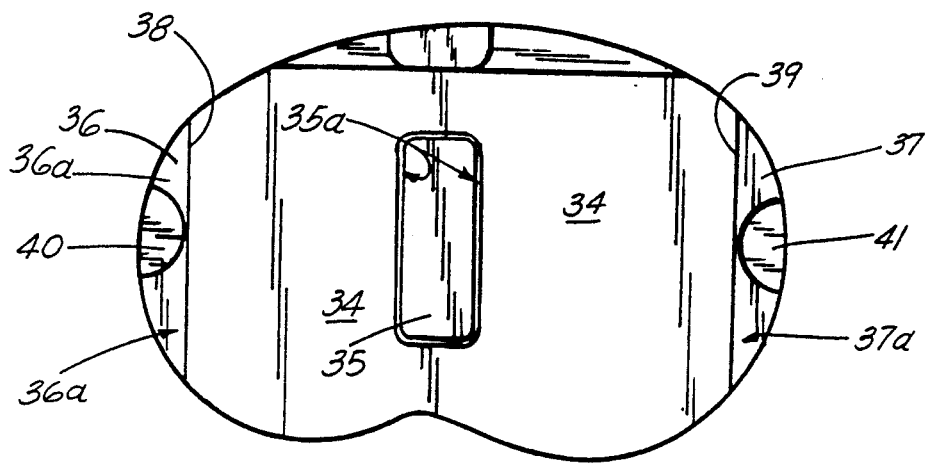
FIG. 7 is a bottom fragmentary view of the preferred embodiment of the apparatus of the present invention.

Because the feet 36, 37 are the only contact between the tibial component insert 25 and the tray 16, the feet act as end supports for the tibial component insert 25. It should be understood that the gap 45 can be sized to allow for more or less deflection. Further, the tibial component insert 25 can be sized and or made of selective materials to control the degree of flexibility desired. Further, the feet can be made larger or smaller so as to control the distance between the feet 36, 37 and thus also control to a degree the amount of flexion achieved between the underside 34 of the component 25 and the top surface 44 of the tibial component 16. In FIG. 6, each foot communicates on its inside surface with the gap 45 by providing generally vertical inside shoulders 37, 38.

Each foot 36, 37 provides a locking tab 40, 41 respectively which registers in recesses 42, 43 respectively on the top surface 44 of plate 17 of tibial component tray 16. The locking tabs 40, 41 in combination with their recesses 42, 43 prevent rotation about a vertical axis of the tibial component 25 with respect to the tibial component tray 16.

Figure 8:
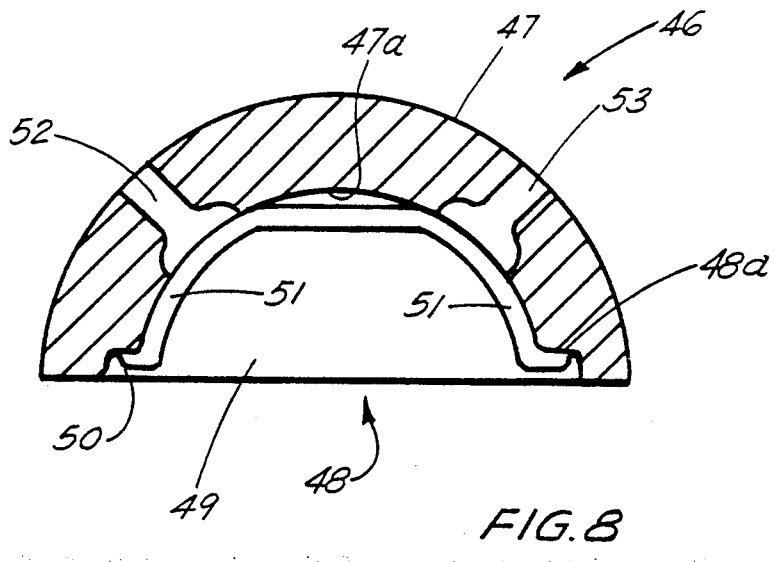
FIGS. 8-10 are fragmentary views of a second embodiment of the apparatus of the present invention illustrating an acetabular joint prosthesis.
Figure 9:
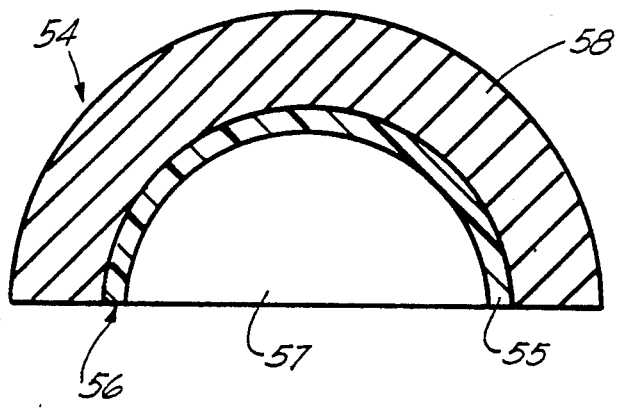
Figure 10:
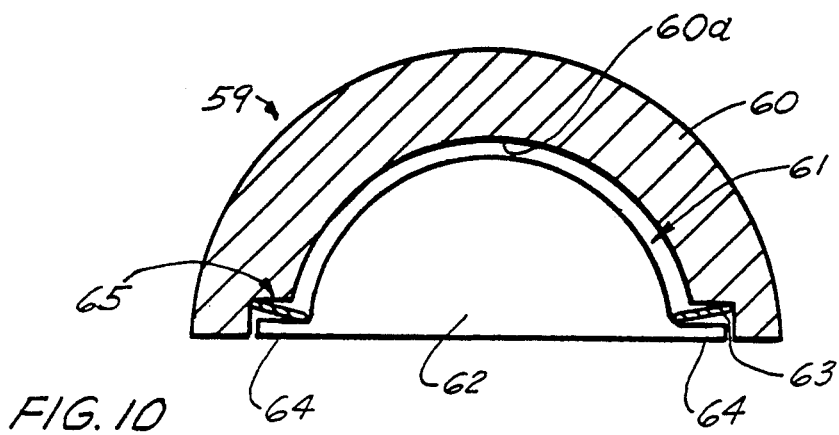

FIGS. 8-10 illustrate an alternate embodiment of the apparatus of the present invention, designated generally by the numeral 46 and in the form of an acetabular prosthesis. Acetabular prosthesis 46 includes a metal back 47 which is hemispherical and hollowed to provide a hemispherical socket 48 that holds a hemispherically shaped polymer liner 49. The liner 49 similarly has a hemispherical socket that is sized to hold the acetabular ball of a hip prosthesis. Polymer liner 49 has an annular flange 50 that registers upon and fits against the inside concave hemispherical socket 48 at annular shoulder 48a. The annular flange 50 forms the connection between liner 49 and metal back 47 thus producing a gap 51. Thus, the liner can flex toward the inside surface 47a of metal back 47. Openings 52 and 53 in FIG. 8 are bone screw openings which allow metal back 47 to be attached to the surrounding bone structure.

In FIG. 9, acetabular prosthesis 54 includes an elastomeric member 55 between the polymer liner 57 and metal back 58. In the embodiment of FIG. 9, the polymer liner 57 flexes toward the metal back 58 allowing deflection between the hip prosthesis and the metal back 58.

In the embodiment of FIG. 10, acetabular prosthesis 59 has a metal back 60 with an inner concave face 60a. A gap 61 is formed between surface 60a and the convex surface 62a of polymer liner 62. An annular flange 64 extends around liner 62 as shown in FIG. 10. A spring washer 63, which is an annular spring washer, extends around flange 64, forming a connection between flange 64 of polymer liner 62 and annular shoulder 65 of metal back 60. The gap 61 between metal back 60 and polymer liner 62 provides an area that the liner 62 can move into and occupy as the spring 63 deflects during use.

TABLE 1

| PART NO. | PARTS LIST DESCRIPTION |
|---|---|
| 10 | knee prosthesis |
| 11 | femur |

TABLE 1-continued

| PART NO. | PARTS LIST DESCRIPTION |
|---|---|
| 12 | tibia |
| 13 | distal end femur |
| 14 | proximal end tibia |
| 15 | femoral component |
| 16 | tibial component tray |
| 17 | plate |
| 18 | stem |
| 19 | post |
| 20 | post |
| 21 | shoulder |
| 22 | flange |
| 23 | articulating femoral surface |
| 24 | articulating femoral surface |
| 25 | tibial component insert |
| 26 | anterior side |
| 27 | posterior side |
| 28 | medial |
| 29 | lateral |
| 30 | tibial articular surface |
| 31 | concavity |
| 32 | concavity |
| 34 | flat surface |
| 35 | socket |
| 35a | shoulder |
| 36 | foot |
| 36a | bearing surface |
| 37 | foot |
| 37a | bearing surface |
| 38 | shoulder |
| 39 | shoulder |
| 40 | locking tab |
| 41 | locking tab |
| 42 | recess |
| 43 | recess |
| 44 | top surface of plate |
| 45 | gap |
| 46 | acetabular prosthesis |
| 47 | metal back |
| 47a | inside surface |
| 48 | hemispherical socket |
| 49 | polymer liner |
| 50 | annular flange |
| 51 | gap |
| 52 | opening |
| 53 | opening |
| 54 | acetabular prosthesis |
| 55 | elastomeric member |
| 56 | gap |
| 57 | polymer liner |
| 58 | metal back |
| 59 | acetabular prosthesis |
| 60 | metal back |
| 60a | concave surface |
| 61 | gap |
| 62 | polymer liner |
| 63 | spring washer |
| 64 | annular flange |
| 65 | annular shoulder |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A knee prosthesis comprising:
   a) a tibial component comprising a tray having a bone engaging surface and an opposite insert engaging surface, and an insert having a bottom surface for engaging said insert engaging surface; and
   b) wherein bottom surface has a recess that defines a gap between the tray and said insert which allows the insert to flex so as to act as a shock absorber for reducing impact loads transmitted through the implant to the bone.

2. The apparatus of claim 1 further comprising a femoral component having femoral articular surfaces that engage the shock absorbing layer means above the gap.

3. The tibial component of claim 1 wherein the tibial insert further comprises a polymeric insert affixed to the tray.

4. The tibial component of claim 3 wherein the polymeric insert has at least one concave articulating surface thereon that is configured to engage the femoral articular surface.

5. The tibial component of claim 4 wherein the articulating surface comprises a pair of concave surfaces configured to engage the femoral articular surface.

6. A knee prosthesis comprising:
a) a tibial component that includes a tray for attachment to the tibia and a tibial insert for articulation against a femoral component;
b) wherein the tray has a bottom surface;
c) a recess that defines a gap between the tray and the insert which allows the insert to flex at the gap when compression load is applied thereto; and
d) a pair of spaced apart feet extending from the bottom surface, each foot having a bearing surface that transmits load between the insert and tray.

7. The knee prosthesis of claim 6 further comprising locking tabs that extend from the feet into the tray.

8. The knee prosthesis of claim 3 wherein the tray includes a flat, laterally extended tray having a generally flat upper surface.

9. A knee prosthesis comprising:
a) a tibial component that includes a tray having a bone engaging surface and an opposite insert engaging surface, and a tibial inset for articulation against a femoral component, said insert having a bottom surface for engaging said insert engaging surface;
b) wherein said tibial component has a recess that defines a gap between said insert engaging surface and said bottom surface which allows the insert to flex at the gap when compression load is applied thereto.

* * * * *